US009095644B2

(12) United States Patent
Yao et al.

(10) Patent No.: US 9,095,644 B2
(45) Date of Patent: Aug. 4, 2015

(54) FLUID COLLECTOR

(75) Inventors: Nan-Kuang Yao, New Taipei (TW);
Jhy-Wen Wu, New Taipei (TW);
Luo-Hwa Miau, New Taipei (TW);
Jen-Chien Chien, New Taipei (TW);
Shi-Fu Chen, New Taipei (TW);
Li-Ling Li, New Taipei (TW)

(73) Assignee: APEX MEDICAL CORP., New Taipei (TW)

( * ) Notice: Subject to any disclaimer, the term of this patent is extended or adjusted under 35 U.S.C. 154(b) by 677 days.

(21) Appl. No.: 13/445,987

(22) Filed: Apr. 13, 2012

(65) Prior Publication Data

US 2013/0274718 A1    Oct. 17, 2013

(51) Int. Cl.
*A61M 1/00* (2006.01)

(52) U.S. Cl.
CPC ........... *A61M 1/0001* (2013.01); *A61M 1/0031* (2013.01); *A61M 1/0088* (2013.01); *A61M 2205/18* (2013.01); *A61M 2205/3334* (2013.01); *A61M 2205/3382* (2013.01)

(58) Field of Classification Search
CPC ....... A61M 1/00; A61M 27/00; A61M 31/00; F16K 15/00; F16K 15/08
USPC ................................. 604/317, 319
See application file for complete search history.

(56) References Cited

U.S. PATENT DOCUMENTS 3,420,493 A * 1/1969 Kraft ............................... 251/82
2006/0122575 A1 * 6/2006 Wakabayashi ................ 604/541

FOREIGN PATENT DOCUMENTS

WO          WO 0142693 A2 *  6/2001

* cited by examiner

*Primary Examiner* — Melanie Hand
(74) *Attorney, Agent, or Firm* — Hsiu-Ming Saunders; Intellectual Property Connections, Inc.

(57) ABSTRACT

A fluid collector has a container, a T-tube, a first screw unit and a second screw unit. The T-tube is connected to the container and has a main pipe and a branch pipe. The first screw unit is mounted in an outlet end of the main pipe. The second screw unit is mounted in a connecting end of the branch pipe, which is connected to the main pipe. The branch pipe has a detecting opening far from the connecting end and connects to a detecting device. By changing the length of the first and second screw units, different detecting values of the pressure are adjusted according to containers with different capacities. Moreover, with the flowing resistance resulting from the first and second screw units, different pressure variations are performed when liquid or air passes through the T-tube. Therefore, massive hemorrhage is clearly identified to keep the patient safe.

12 Claims, 7 Drawing Sheets

FLUID COLLECTOR

BACKGROUND OF THE INVENTION

1. Field of the Invention

The present invention relates to a fluid collector, especially to a fluid collector used for a negative pressure wound therapy system to collect the pus and the infection subjects.

2. Description of the Prior Arts

Fluid collectors are widely used for medical devices to collect the pus and the infection subjects. For different needs, fluid collectors in the same medical device may have different sizes. Since these medical devices need to have detecting units to detect whether the fluid collectors are full, the fluid collectors with different sizes need different detecting parameters. Therefore, once the medical devices use different fluid collectors with different sizes or capacities, the detecting parameters of the medical devices need to be adjusted accordingly. Adjusting detecting parameters involves modifying software and hardware so that adjusting detecting parameters is complicated.

For example, negative pressure wound therapy utilizes wound sheets, soft suction pads, or biocompatible porous materials to attach on the wounds and connect to a vacuum pump. The vacuum pump creates negative pressure in the wound to extract the pus and infection subjects and to draw the healthy tissue fluid so that a moist therapy environment is maintained. Therefore, the blood circulation around the wound is promoted to accelerate wound healing. To provide negative pressure wound therapy, a conventional negative pressure wound therapy system has been developed. The system extracts pus and the infection subjects into the conventional fluid collector. The detecting unit of the system detects the pressure in the conventional fluid collector to determine whether the conventional fluid collector is full. When the conventional fluid collector is full, the system alarms to remind the user to change for an empty fluid collector.

When the patient stays in the hospital, the patient needs not to move frequently so that a large fluid collector is suitable to reduce frequency of changing the conventional fluid collector. When the patient stays at home or goes out, a small fluid collector is suitable to be carried easily. The conventional fluid collectors of different sizes need different system parameters, such that different pressures are reached when the different fluid collectors are full. Therefore, the detecting unit has to detect different values. However, the conventional system does not have devices to adjust the parameters of the detecting unit. Thus, the conventional fluid collectors with different sizes cooperate with different systems with different parameters. Then the patients have to use and get adjusted to different systems when they stay at different places.

In addition, the U.S. Food and Drug Administration (FDA) repeatedly warns about the negative pressure wound therapy that may cause many adverse effects. The worst problem is accidentally bleeding during the negative pressure wound therapy. Since 2007, the accidental bleeding has caused 12 deaths and 174 injuries. The great parts of those cases occur at home or in a long-term care facility where the patients do not have personal care assistants or nurses around frequently. Once the wound bleeds accidentally, massive hemorrhage may quickly occur via the negative pressure and cause tragedy.

The vacuum pump has to extract the air in the fluid tubes when the negative wound therapy system is operated, and then extracts pus. Even the negative pressure in the system is stable during the therapy, much air may still be released from the wound sheet. Thus, air and liquid are mixed in the fluid tubes of the negative wound therapy system during the negative pressure therapy.

The conventional negative pressure wound therapy systems has a rigid collector connecting to a front end of the vacuum pump to extract the pus and the infection subjects into the rigid collector through the fluid tube. Although the air and the liquid are separated certainly because of the gravity, it is unable to determine whether the air or liquid flows into the rigid collector. Therefore, the conventional negative pressure wound therapy system cannot detect bleeding continuously since it is unable to determine whether the air or liquid flows in the fluid tubes. Then the patients are in danger because the conventional system cannot alarm while massive hemorrhage occurs.

To overcome the shortcomings, the present invention provides a fluid collector to mitigate or obviate the aforementioned problems.

SUMMARY OF THE INVENTION

The main objective of the present invention is to provide a fluid collector with an adjusting assembly. The fluid collector has a container, a T-tube, a first screw unit and a second screw unit. The T-tube is connected to the container and has a main pipe and a branch pipe. The first screw unit is mounted in an outlet end of the main pipe. The second screw unit is mounted in a connecting end of the branch pipe, which is connected to the main pipe. The branch pipe has a detecting opening far from the connecting end and connects to a detecting device. By changing the length of the first and second screw units, different detecting values of the pressure are adjusted according to containers with different capacities. Moreover, with the flowing resistance resulting from the first and second screw units, different pressure variations are performed when liquid or air passes through the T-tube. Therefore, massive hemorrhage is clearly identified to keep the patient safe.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
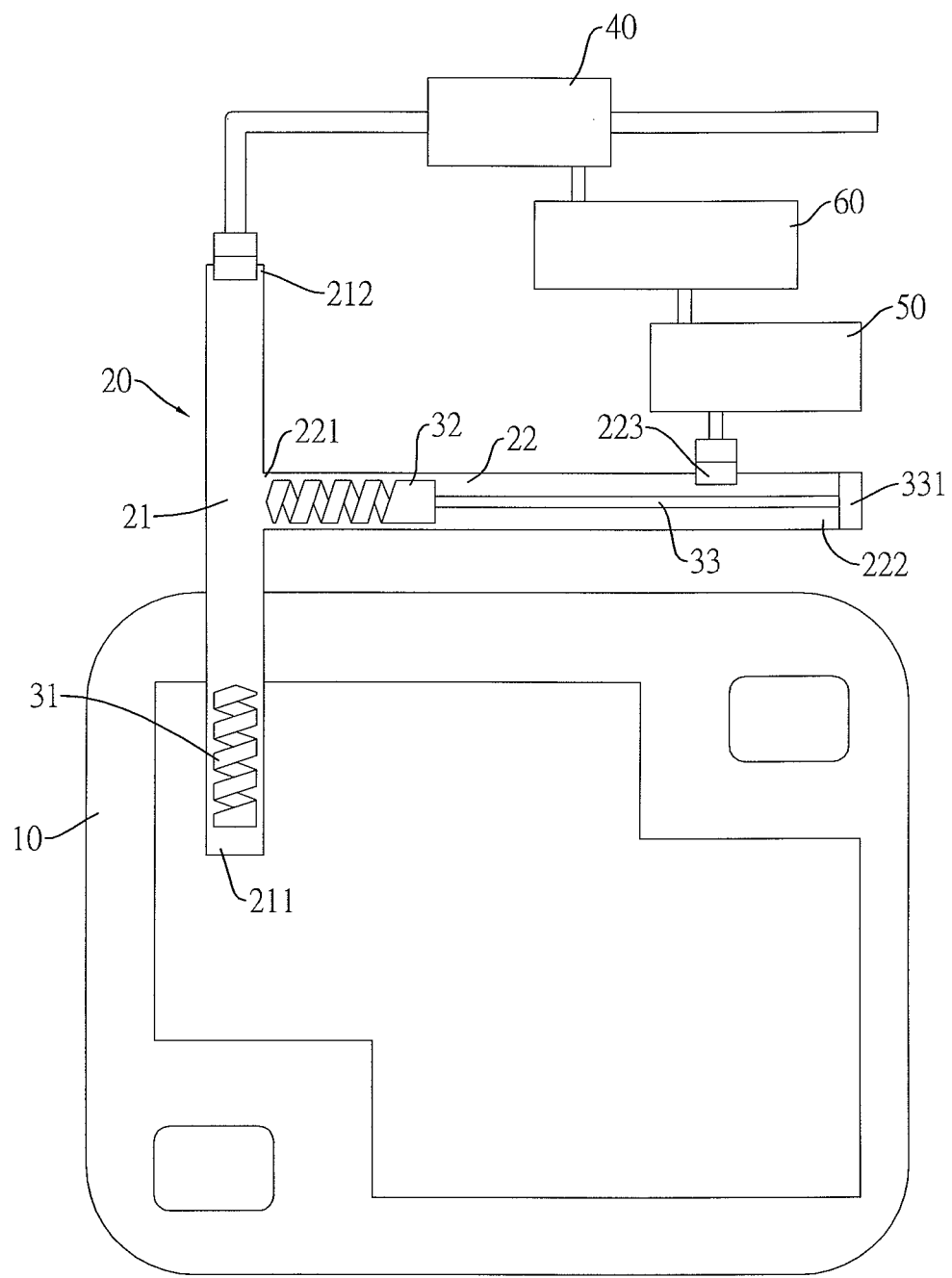
FIG. 1 is an illustrating view of a fluid collector in accordance with the present invention mounted in a negative pressure wound therapy system.
Figure 2:
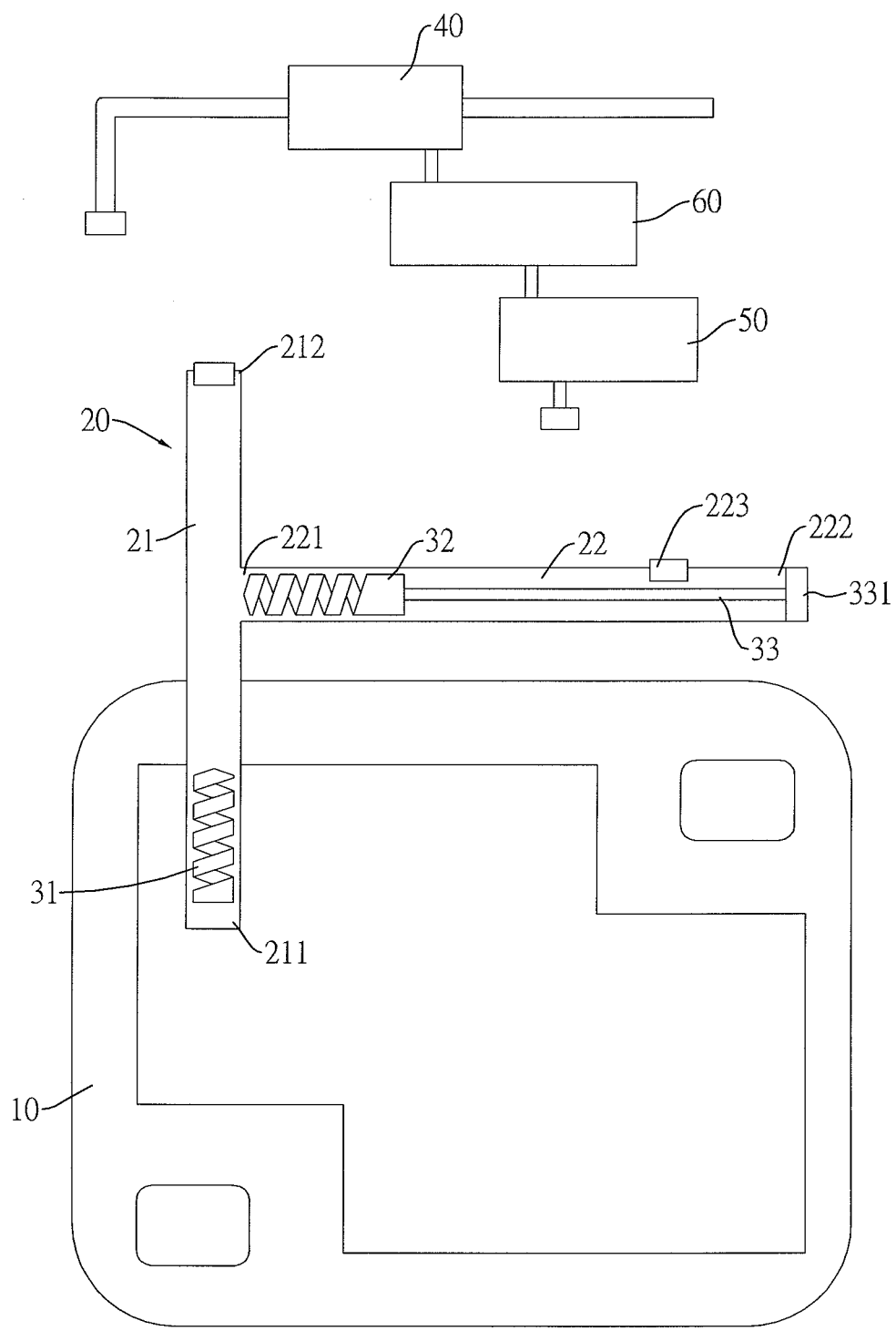
FIG. 2 is an exploded view of the negative pressure wound therapy system in FIG. 1.

With reference to FIGS. 1 and 2, a fluid collector in accordance with the present invention comprises a container 10, a T-tube 20 and a screw adjusting assembly.

The container 10 has an opening and may be a rigid box or a soft bag. Using the soft bag can reduce volume and lighten the weight so that the container 10 is easily carried. Moreover, the soft bag can be used in any orientation so that even when the patient is lying on the bed, the soft bag is still easily used.

The T-tube 20 is connected to the opening of the container 10 and has a main pipe 21 and a branch pipe 22. The main pipe 21 has an outlet end 211 and an inlet end 212. The outlet end 211 is connected to and communicates with the opening of the container 10. The branch pipe 22 is attached transversely to a sidewall of the main pipe 21 and communicates with the main pipe 21. In a preferred embodiment, the branch pipe 22 is transversely mounted securely on the sidewall of the main pipe 21, or is formed transversely on and protrudes out from the sidewall of the main pipe 21. The branch pipe 22 has a connecting end 221, an opening end 222 and a detecting opening 223. The connecting end 221 of the branch pipe 22 is attached to the main pipe 21. The detecting opening 223 is formed through the sidewall of the branch pipe 22 and is located far from the connecting end 221 of the branch pipe 22.

The screw adjusting assembly is mounted in the T-tube 20 and comprises a first screw unit 31, a second screw unit 32 and an extending rod 33. The first screw unit 31 is mounted in the outlet end 211 of the main pipe 21. The second screw unit 32 is mounted in the connecting end 221 of the branch pipe 22. The extending rod 33 is formed on a distal end of the second screw unit 32 and has an enlarged head 331. The enlarged head 331 is formed on a distal end of the extending rod 33, is plugged in and seals the opening end 222 of the branch pipe 22. The enlarged head 331 may be formed around the distal end of the extending rod 33.

With reference to FIG. 1, the fluid collector as described is used for medical instrument to collect medical waste fluid. For example, the fluid collector as described is used in a negative pressure wound therapy system. The inlet end 212 of the main pipe 21 is connected to the pump 40 to receive the air or the liquid from the wound. The detecting opening 223 of the branch pipe 22 is connected to the pressure-detecting device 50. The pump 40 and the pressure-detecting device 50 are connected electrically to the controller 60.

When the fluid containing air and liquid is pumped into the inlet end 212 of the main pipe 21, the fluid flows along the screws of the first and second screw units 31, 32 so that the flowing path is extended while the main and branch pipes 21, 22 are short. Therefore, the fluid with air and liquid is organized while passing through the first and second screw units 31, 32 to result in pressure difference between the outlet end 211 of the main pipe 21 and the detecting opening 223 of the branch pipe 22. The pressure-detecting device 50 detects the pressure at the detecting opening 223 and obtains the pressure variation in the container 10 to determine some events, such as filling of the container 10, pressurized abnormally of the container 10, abnormally of the flow, or disengage of the connection of the pipes.

Figure 3:
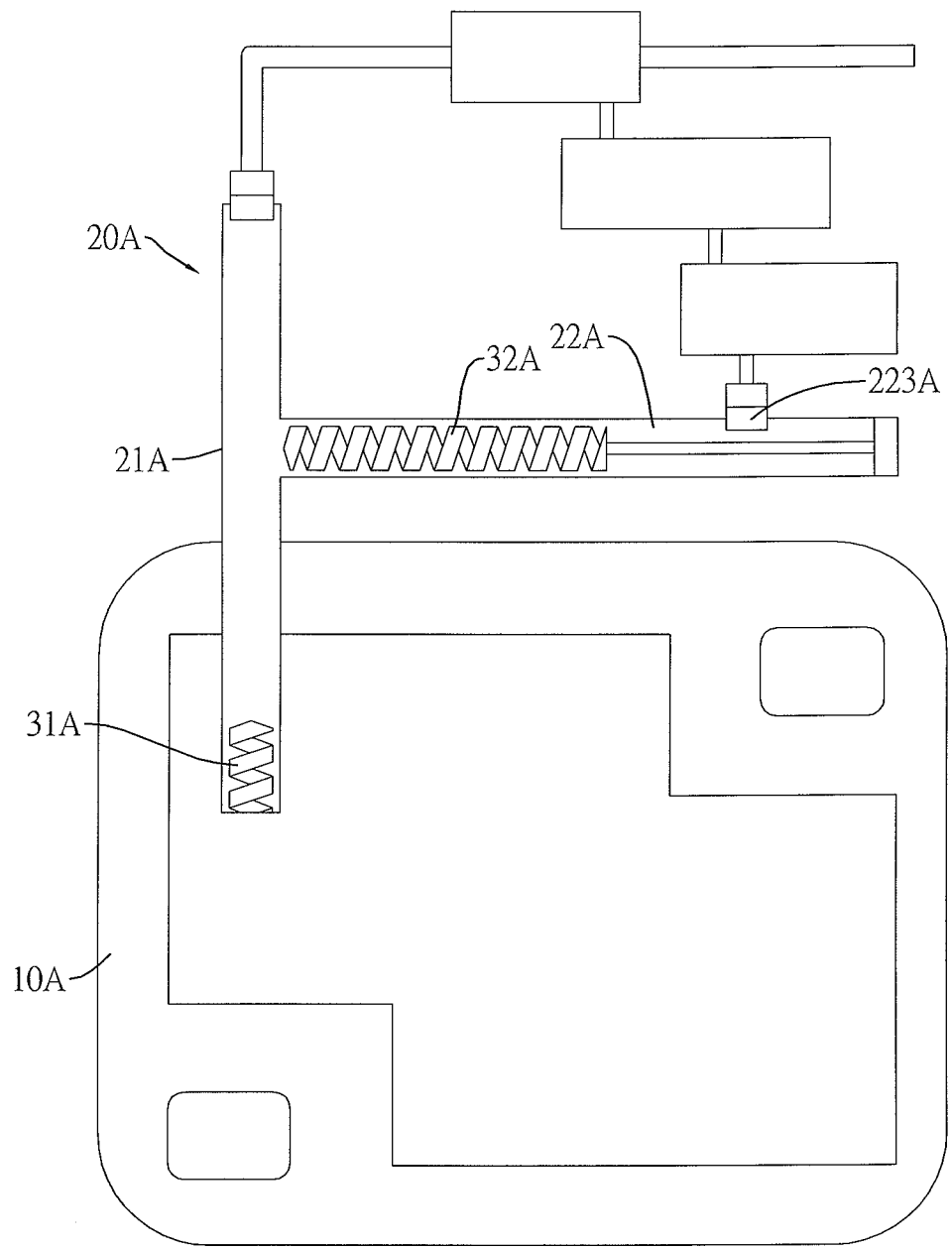
FIG. 3 is an illustrating view of another embodiment of a fluid collector in accordance with the present invention.

With reference to FIG. 3, the first screw unit 31A is shorter than the second screw unit 32A so that the second screw unit 32A provides larger flow resistance. Since the flow resistance that flows toward the detecting opening 223A is larger, the air flows toward the detecting opening 223A is less than the air flows toward the container 10A. Then the pressure is raised slower at the detecting opening 223A so that the pressure at the detecting opening 223A is deferred to reach the predetermined pressure showing that the container 10A is full. Therefore, the container 10A receives more fluid, and the negative pressure wound therapy system can use the container 10A with larger capacity.

Figure 4:
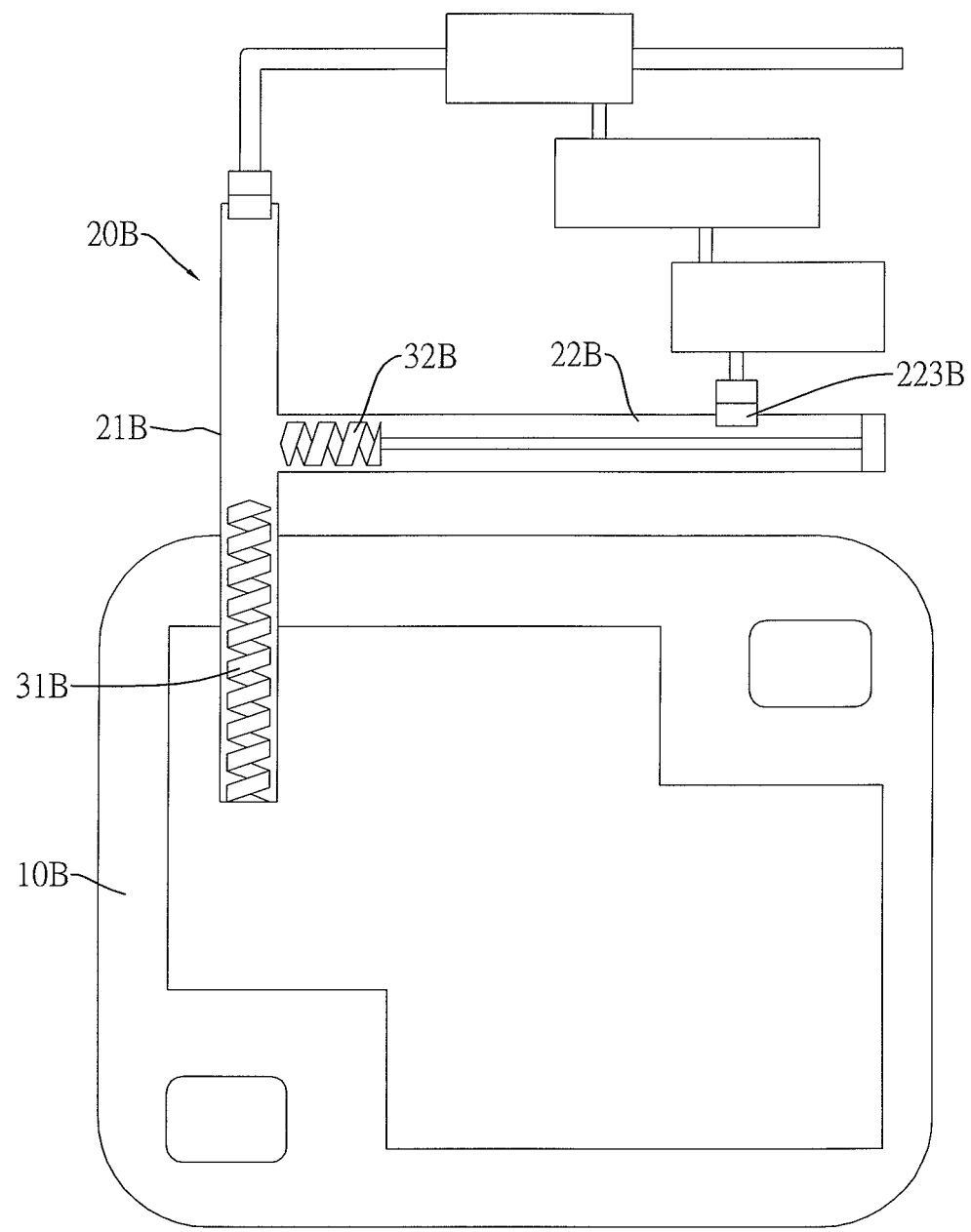
FIG. 4 is an illustrating view of still another embodiment of a fluid collector in accordance with the present invention.

With reference to FIG. 4, the first screw unit 31B is longer than the second screw unit 32B so that the second screw unit 32B provides smaller flow resistance. Since the flow resistance that flows toward the detecting opening 223B is smaller, the air flowing toward the detecting opening 223B is more than the air flowing toward the container 10B. Then the pressure is raised quicker at the detecting opening 223B so that the pressure at the detecting opening 223B is faster to reach the predetermined pressure showing that the container 10B is full. Therefore, the container 10B receives less fluid, and the negative pressure wound therapy system can use the container 10B with less capacity.

Thus, the medical care personnel or patients may choose the containers with appropriate screw units based on desired capacity. The parameters of the negative pressure wound therapy system do not need to be adjusted to enhance the convenience.

Figure 5:
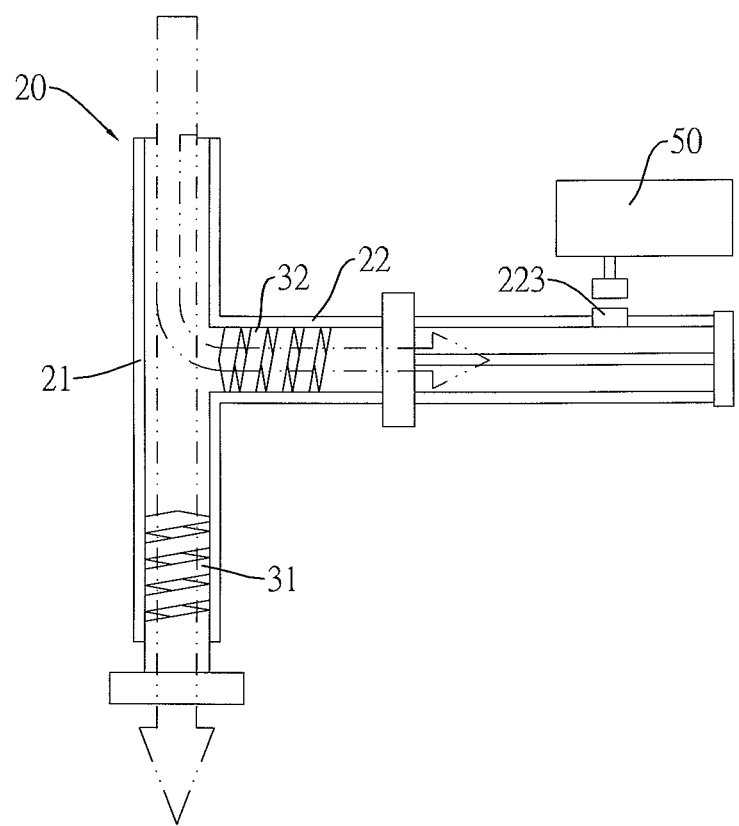
FIG. 5 is an operational illustrating view of the fluid collector in FIG. 1.

Moreover, with reference to FIG. 5, the T-tube 20 has no liquid inside and air is infused into the T-tube 20. According to law of partial pressures, flow resistance influences flow rate. The pressure at the detecting opening 223 is gradually raised to a stable pressure.

Alternatively, the liquid is infused continually. Most of the liquid is resisted in the first and second screw units 31, 32 and only a little of the liquid flows into the container 10. The T-tube 20 becomes airtight temporally. According to Pascal's principle, the pressure vector is regard as scalar. Therefore, the pressure detected at the detecting opening 223 is raised rapidly as being direct proportional to the quantity of the fused liquid.

Figure 6:
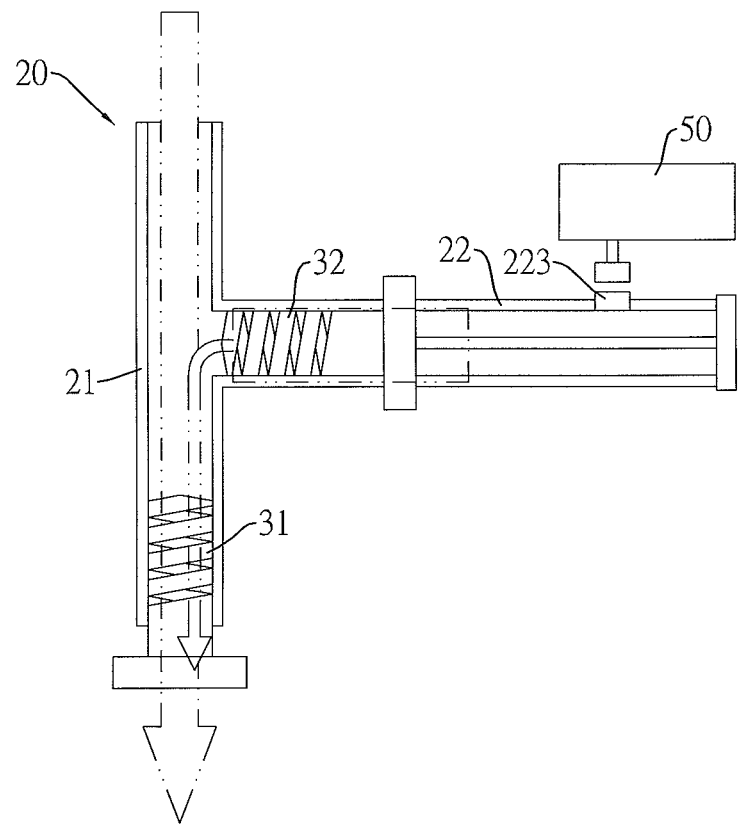
FIG. 6 is an operational illustrating view of the fluid collector in FIG. 1.

With reference to FIG. 6, the T-tube 20 has liquid inside and air is infused into the T-tube 20. The liquid in the main pipe 21 is pushed out firstly and some liquid remains at the detecting opening 223 of the branch pipe 22. The flowing air in the main pipe 21 results in Bernoulli effect and forms low pressure. Then the liquid remaining in the branch pipe 22 is sucked out gradually to result in the pressure at the detecting opening 223 steadily lower down.

Figure 7:
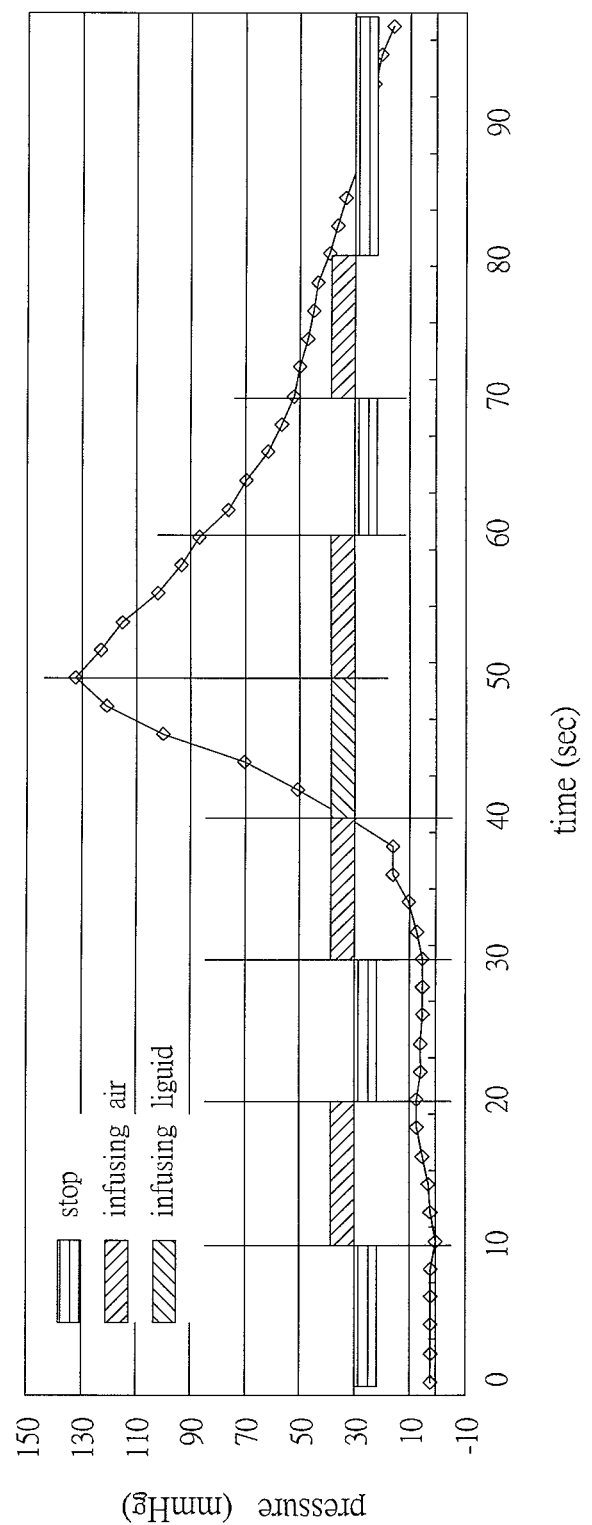
FIG. 7 is a graph depicting time plotted against pressure of the fluid collector in FIG. 1.

With reference to FIG. 7, an experiment to alternatively infuse air, liquid or stop infusing into the fluid collector as described by manually controlling the pump is operated and the pressure variation at the detecting opening of the branch pipe is recorded. Based on aforementioned laws and principles, the pressure is raised rapidly only when infusing liquid. Therefore, with the fluid collector as described, the user can determine whether the fluid in the T-tube is liquid or air and can identify if massive hemorrhage occurs. Thus, the patient is kept safe.

With further reference to FIG. 1, the fluid collector as described is used in the negative pressure wound therapy system. When the massive hemorrhage occurs and lots of blood flows into the T-tube 20, the pressure at the detecting opening 223 is raised rapidly. The controller 60 shuts down the pump 40 immediately and alarms to inform the user.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:
1. A fluid collector comprising:
a container having an opening;

a T-tube connected to the opening of the container and having
    a main pipe having
        an outlet end connected to and communicating with the opening of the container; and
        an inlet end; and
    a branch pipe attached transversely to a sidewall of the main pipe, communicating with the main pipe and having
        a connecting end attached the main pipe;
        an opening end; and
        a detecting opening formed through the sidewall of the branch pipe and located closer to the opening end than to the connecting end of the branch pipe; and
a screw adjusting assembly mounted in the T-tube and comprising
    a first screw unit mounted in the outlet end of the main pipe; and
    a second screw unit mounted in the connecting end of the branch pipe.

2. The fluid collector as claimed in claim 1, wherein the first screw unit is longer than the second screw unit.

3. The fluid collector as claimed in claim 1, wherein the first screw unit is shorter than the second screw unit.

4. The fluid collector as claimed in claim 1, wherein the container is a soft bag.

5. The fluid collector as claimed in claim 2, wherein the container is a soft bag.

6. The fluid collector as claimed in claim 3, wherein the container is a soft bag.

7. The fluid collector as claimed in claim 1, wherein the screw adjusting assembly comprises an extending rod formed on a distal end of the second screw unit and having an enlarged head formed on a distal end of the extending rod and plugged in and sealing the opening end of the branch pipe.

8. The fluid collector as claimed in claim 2, wherein the screw adjusting assembly comprises an extending rod formed on a distal end of the second screw unit and having an enlarged head formed on a distal end of the extending rod and plugged in and sealing the opening end of the branch pipe.

9. The fluid collector as claimed in claim 3, wherein the screw adjusting assembly comprises an extending rod formed on a distal end of the second screw unit and having an enlarged head formed on a distal end of the extending rod and plugged in and sealing the opening end of the branch pipe.

10. The fluid collector as claimed in claim 4, wherein the screw adjusting assembly comprises an extending rod formed on a distal end of the second screw unit and having an enlarged head formed on a distal end of the extending rod and plugged in and sealing the opening end of the branch pipe.

11. The fluid collector as claimed in claim 5, wherein the screw adjusting assembly comprises an extending rod formed on a distal end of the second screw unit and having an enlarged head formed on a distal end of the extending rod and plugged in and sealing the opening end of the branch pipe.

12. The fluid collector as claimed in claim 6, wherein the screw adjusting assembly comprises an extending rod formed on a distal end of the second screw unit and having an enlarged head formed on a distal end of the extending rod and plugged in and sealing the opening end of the branch pipe.

* * * * *